United States Patent [19]
Weinkauf et al.

[11] Patent Number: 6,007,829
[45] Date of Patent: Dec. 28, 1999

[54] COSMETIC SKIN CARE COMPOSITIONS CONTAINING SUCCINATE COMPOUNDS

[75] Inventors: Ronni Weinkauf, River Edge; Uma Santhanam, Tenafly; Laura Rose Palanker, Jackson; Allan Robert Burger, Passaic, all of N.J.; Anthony Vincent Rawlings, Warrington, United Kingdom

[73] Assignee: Cheesebrough-Pond's USA Co., Greenwich, Conn.

[21] Appl. No.: 09/213,496

[22] Filed: Dec. 17, 1998

[51] Int. Cl.⁶ ...................................................... A61K 7/02
[52] U.S. Cl. .......................... 424/401; 514/937; 514/938; 424/70.1; 424/70.19; 424/70.21; 424/70.22; 424/70.31
[58] Field of Search ................................... 424/401, 70.1, 424/70.19, 70.22, 70.21, 70.31

[56] References Cited

U.S. PATENT DOCUMENTS

| | | | |
|---|---|---|---|
| 3,976,781 | 8/1976 | Kalopisis | 424/309 |
| 5,047,166 | 9/1991 | Weil | 252/132 |
| 5,149,522 | 9/1992 | Schwarz et al. | 424/70 |
| 5,169,622 | 12/1992 | Kopolow et al. | 424/47 |
| 5,236,710 | 8/1993 | Guerroro et al. | 424/401 |
| 5,696,288 | 12/1997 | Gutierrez et al. | 562/583 |
| 5,705,147 | 1/1998 | Shapiro et al. | 424/70.1 |
| 5,747,049 | 5/1998 | Tominaga | 424/401 |

*Primary Examiner*—Thurman K. Page
*Assistant Examiner*—Alysia Berman
*Attorney, Agent, or Firm*—Rimma Mitelman

[57] ABSTRACT

Cosmetic skin care compositions containing succinate compounds and cosmetic method of improving the appearance of wrinkled, lined, dry, flaky, aged or photodamaged skin and improving skin thickness, elasticity, flexibility, radiance, glow and plumpness.

3 Claims, No Drawings

COSMETIC SKIN CARE COMPOSITIONS CONTAINING SUCCINATE COMPOUNDS

FIELD OF THE INVENTION

Cosmetic compositions containing succinate compounds and the use of the compositions for improving the appearance and cosmetic condition of the skin.

BACKGROUND OF THE INVENTION

Cosmetic products which improve the appearance of skin are increasingly popular with consumers. These products aim to alleviate or delay the signs of aged or photoaged skin, such as fine lines and wrinkles, dry and sagging skin. Although the marketplace offers a variety of products, the cosmetic manufacturers continue the quest for alternative actives, in order to provide a consumer with a choice of products.

Several patents disclose cosmetic compositions incorporating succinate derivatives, but the disclosed compounds differ structurally from the succcinate compounds included in the present invention. See for instance Kalopissis (U.S. Pat. No. 3,976,781), Kopolow (U.S. Pat. No. 5,169,622), Shapiro et al. (U.S. Pat. No. 5,705,147), and Weil (U.S. Pat. No. 5,047,166). Gutierrez et al. (U.S. Pat. No. 5,696,288) discloses oxydisuccinate in detergent compositions.

Cosmetic compositions containing succinic acid are known. Unfortunately, succinic acid has limited solubility in water and is therefore hard to formulate in cosmetic compositions such as water-in-oil emulsions at sufficiently high levels. For ease of formulation, it is advantageous to have a more water-soluble active.

The present invention is based at least in part on the discovery that specific highly water-soluble succinate compounds increase glycosaminoglycan and collagen synthesis in the skin cells.

SUMMARY OF THE INVENTION

The present invention includes a skin care composition comprising:
(a) a succinate compound selected from the group consisting of sulfosuccinic acid or a salt thereof, 2,2'-oxydisuccinic acid or a salt thereof, ethylene glycol disuccininc acid or a salt thereof, and mixtures thereof in an amount of from about 0.05 to about 40 wt. %; and
(b) a cosmetically acceptable vehicle.

Preferably, the composition is a water-in-oil emulsion, containing the succinate compound in an aqueous phase, in order to improve its penetration through the skin.

The present invention also includes a cosmetic method of improving or preventing the condition of wrinkled, lined, dry, flaky, aged or photodamaged skin and improving skin thickness, elasticity, flexibility, radiance, glow and plumpness, which method includes applying to the skin the inventive composition. Cosmetic compositions of the invention are intended for topical application to mammalian skin which is already dry, flaky, lined, wrinkled, aged, photodamaged, or the inventive compositions may be applied prophylactically to normal healthy skin to prevent or reduce the deteriorative changes.

The composition may be used in a cosmetic method to improve the production of collagen and/or glycosaminoglycans by fibroblasts.

The following detailed description and the examples illustrate some of the effects of the inventive compositions. The invention and the claims, however, are broader than the problems solved and are not limited thereto.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, hands, legs, feet and scalp.

For the avoidance of doubt the word 'comprising' is intended to mean including but not necessarily consisting of or composed of. In other words the listed steps or options need not be exhaustive.

The succinate compound included in the present invention is selected from the group consisting of sulfosuccinic acid, 2,2'-oxydisuccinic acid, ethylene glycol disuccinic acid, having the following chemical structures:

Sulfosuccinic acid:

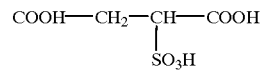

Oxydisuccinic acid:

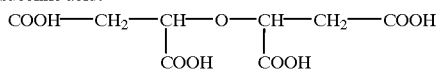

Ethylene glycol disuccinic acid:

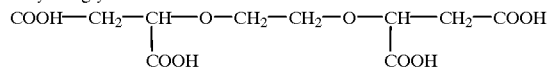

Depending on the pH of the composition, these compounds may be present in the form of the salts, e.g. potassium or sodium or ammonium salts.

The succinate compound is used in the inventive compositions in an amount of from 0.05 to 40%, preferably from 2 to 20%, most preferably from 4 to 10%. These succinate compounds may be obtained from Sigma or may be synthesized as described in Gutierrez et al. (U.S. Pat. No. 5,696,288).

The compositions according to the invention also comprise a cosmetically acceptable vehicle to act as a dilutant, dispersant or carrier for the succinate compound in the composition, so as to facilitate its distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Optional Skin Benefit Materials and Cosmetic Adjuncts:

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-oxidants, anti-aging ingredients and sunscreens.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

The composition according to the invention is intended primarily as a product for topical application to human skin, especially as an agent for improving skin's resilience and firmness, radiance and clarity and finish, and for preventing or reducing the appearance of lined, wrinkled, dry, aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging:

The cosmetic skin composition of the invention can be in any form, e.g. formulated as a gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

EXAMPLE 1

This example measures production of glycosaminoglycans by fibroblasts in response to treatment with various test compounds.

Glycosaminoglycans (GAGs) are a family of polysaccharides which (with the exception of hyaluronic acid (HA)) can be linked to a protein core, forming a proteoglycan. The main GAGs in the dermis are HA and dermatan sulfate, with chondroitin-4-sulfate and chondroitin-6-sulfate present in small amounts. Made by both keratinocytes and dermal fibroblasts, GAGs are essential components of the extracellular matrix, although they make up only 0.2% of the dry weight of skin. GAGs hydrate in the skin (HA can hold up to 1000x its mass in water) and maintain basement membrane integrity, regulate cellular interactions and nutrient transport, and are involved in collagen and possibly elastic fiber formation. The proportion of GAGs (especially HA) in the dermis has been shown to be diminished with aging. See Perlish et al, "The Role of Glycosaminoglycans in Aging of the Skin." Retinoic acid, the benchmark anti-aging active, has been shown to increase GAG content of the spinous and granular layers of the epidermis and the papillary dermis of aged skin in vivo. See Kligman et al., "Effects of topical tretinoin on non-sun-exposed protected skin of the elderly," J. Am Acad Dermatol 1993;29:25–33.

Protocol for measuring GAGs

Neonatal human dermal fibroblasts were purchased from Clonetics Corp., San Diego, Calif. and used in passages 5–10. All materials for cell culture were purchased from Life Technologies, N.Y. Cells were seeded at a density of approximately 50,000/well in a 12 well plate in DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, each well was rinsed in serum-free DMEM and the cells dosed with test compounds (in triplicate) in 750 $\mu$L of serum-free DMEM at pH 7.4 titrated with NaOH. Test compounds were used at a concentration indicated in Tables 1a–1c below. Controls did not contain any test compounds. After 24 hours, this medium was aspirated and the treatment step repeated. After a second 24-hour period, this medium, containing the soluble GAGs, was collected and frozen until analysis.

A positively-charged Zeta Probe membrane was soaked in sterile water and placed into the Dot-Blot Apparatus (both Bio-Rad Labs, Hercules, Calif.). 100 $\mu$L of water was applied to each well and pulled through using a vacuum. After thawing, 100 $\mu$L of test solution samples was applied to the membrane and allowed to gravity filter (about 1.5–2 hours). GAGs were now bound to membrane. The membrane was blocked in 3% w/v fatty acid free bovine serum albumin (Sigma) in water for one hour. A dye solution of 0.5% w/v Alcian Blue dye (ICN Biochemicals, Cleveland, Ohio) in 3% acetic acid, pH approximately 2.3, was made. The membrane was washed twice in distilled water and then stained in the dye solution on a rotary shaker for 15 minutes. The dye was poured off and the membrane destained twice for 15 minutes each time in 3% acetic acid. The membrane was rinsed in water and left to dry overnight. The Bio-Rad GS 700 Image Analysis Densitometer was used to quantitate the intensity of color in each spot.

Fold increase over control was calculated as a ratio of densitometer reading for cells treated with a test compound over control. p-value was calculated using student's t-test. Dioctyl sulfosuccinate was obtained from Sigma.

The results of three separate experiments are summarized in Tables 1a–1c.

TABLE 1a

| Test Compound | Concentration (mM) | Densitometer reading (average) | Standard Deviation | p-value vs. control | Fold increase over control |
|---|---|---|---|---|---|
| Control | | 0.423 | 0.0320 | | |
| Dioctyl sulfosuccinate | 10 | 0.082 | 0.0178 | 0.0000015 | 0.2 |
| Dioctyl sulfosuccinate | 1 | 0.156 | 0.0358 | 0.000032 | 0.4 |
| Dioctyl sulfosuccinate | 0.1 | 0.145 | 0.00781 | 0.0000028 | 0.3 |
| Sulfosuccinic acid | 10 | 0.554 | 0.0266 | 0.000751 | 1.3* |
| Sulfosuccinic acid | 1 | 0.380 | 0.0293 | 0.096 | 0.9 |
| Sulfosuccinic acid | 0.1 | 0.386 | 0.0377 | 0.187 | 0.9 |

TABLE 1b

| Test Compound | Concentration (mM) | Densitometer reading (average) | Standard Deviation | p-value vs. control | Fold increase over control |
|---|---|---|---|---|---|
| Control | | 0.217 | 0.0138 | | |
| Dioctyl sulfosuccinate | 0.1 | 0.127 | 0.0334 | 0.00244 | 0.6 |
| Dioctyl sulfosuccinate | 0.01 | 0.0898 | 0.0162 | 0.00002 | 0.4 |
| Succinic acid | 10 | 0.195 | 0.0241 | 0.164 | 0.9 |
| Succinic acid | 1 | 0.197 | 0.00872 | 0.0475 | 0.9 |
| Ethylene glycol disuccinate | 10 | 0.305 | 0.0327 | 0.00026 | 1.4* |
| Ethylene glycol disuccinate | 1 | 0.302 | 0.0157 | 0.000185 | 1.4* |
| Oxydisuccinate | 10 | 0.544 | 0.0438 | 0.0000075 | 2.5* |
| Oxydisuccinate | 1 | 0.309 | 0.0199 | 0.000273 | 1.4* |
| Oxydisuccinate | 0.1 | 0.199 | 0.0677 | 0.607 | 0.9 |
| Sulfosuccinic acid | 10 | 0.261 | 0.012702 | 0.00343 | 1.2* |
| Sulfosuccinic acid | 1 | 0.232 | 0.0180 | 0.233 | 1.1 |

TABLE 1c

| Test Compound | Concentration (mM) | Densitometer reading (average) | Standard Deviation | p-value vs. control | Fold increase over control |
|---|---|---|---|---|---|
| Control | | 0.336 | 0.0242 | | |
| Succinic acid | 10 | 0.371 | 0.0188 | 0.0610 | 1.1 |
| Succinic acid | 1 | 0.311 | 0.0372 | 0.303 | 0.9 |
| Ethylene glycol disuccinate | 10 | 0.287 | 0.0266 | 0.0338 | 0.9 |
| Ethylene glycol disuccinate | 1 | 0.500 | 0.0192 | 0.000042 | 1.5* |
| Oxydisuccinate | 10 | 0.532 | 0.123 | 0.0203 | 1.6* |
| Oxydisuccinate | 1 | 0.583 | 0.0136 | 0.000002 | 1.7* |
| Sulfosuccinic acid | 10 | 0.455 | 0.0517 | 0.00594 | 1.4* |
| Sulfosuccinic acid | 1 | 0.275 | 0.0122 | 0.00395 | 0.8 |

The results in Tables 1a–1c demonstrate that sulfosuccinate, ethylene glycol disuccinate and oxydisuccinate significantly increased GAG production by fibroblasts. Dioctyl sulfosuccinate (not within the scope of the present claims) had the effect of decreasing GAG production.

EXAMPLE 2

This example measured production of procollagen I by fibroblasts in response to treatment with various test compounds.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, N.Y. and used in passages 5–10. Cells were seeded at a density of approximately 10,000/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, the medium was removed and cells were washed with serum-free DMEM, and each well dosed with 200 µl of a solution of a test compound in serum-free DMEM at pH 7.4 titrated to NaOH. Each dosing was replicated in a total of six wells. Test compounds were used at concentrations indicated in Tables 2a –2d below. Control did not contain a test compound. After 24 hours, the test compound solution or the control solution was removed and cells redosed with 100 µl of the same solutions. Test compounds were used at concentrations indicated in Table 1 below. After 24 hours, all solutions were removed and stored over the weekend at 4° C. with protease inhibitor (Aprotinin from Sigma) at a concentration of 0.5%. The test compound solution was then diluted in DMEM (approximately 20 µl sample in 200 µl DMEM).

Nitrocellulose membrane and 3 sheets of filter paper were soaked in TRIS buffered saline (TBS, pH 7.3.). BioRad slot blot apparatus (BioRad Labs, Calif.) was set up with 3 sheets filter paper on bottom, membrane on top, and tightened tightened. 100 ml TBS was added per well. Vacuum was used to suck TBS through membrane. The test compound solution or control was vortexed, then 100 µl was loaded per well and gravity filtered. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was washed 3 times for 5 minutes in TBS/0.1% Tween. 3 mL PBS was incubated with 30 µl each of solutions A and B from Vectastain Kit for 30 minutes. The membrane was placed in the resulting solution for 30 minutes in a sealed bag with shaking. The membrane was then removed and washed twice for 5 minutes in TBS/0.1% Tween. The membrane was then stained using the following solution:

12.5 mg 3-amino 9-ethyl carbazole (Sigma); 3.125 (approximately) mL DMF (N,N- dimethylformamide, from Sigma); 21.5 mL 0.2M NaOAc buffer, pH 5.2; 12.5 µl $H_2O_2$ The membrane was stained until color developed and the reaction stopped with 2 washes for 10 minutes in tap water. The blot was scanned on a Bio-Rad GS700 Image Analysis densitometer. Fold increase was calculated as a ratio of densitometer reading for cells treated with a test compound over control.

The results that were obtained are summarized in Tables 2a–2d.

TABLE 2a

| Test Compound | Concen-tration (mM) | Densitometer reading (average) | Standard Deviation | p-value (vs. control) | Fold increase over control |
|---|---|---|---|---|---|
| Control | | 1.11 | 0.567 | | |
| Dioctyl sulfosuccinate | 10 | 0.402 | 0.128 | 0.0562 | 0.4 |
| Dioctyl sulfosuccinate | 1 | 0.685 | 0.451 | 0.0841 | 0.6 |
| Dioctyl sulfosuccinate | 0.1 | 0.469 | 0.196 | 0.0517 | 0.4 |
| Sulfosuccinic acid | 10 | 2.36 | 0.965 | 0.0242 | 2.1* |
| Sulfosuccinic acid | 1 | 1.84 | 0.999 | 0.0443 | 1.7* |
| Sulfosuccinic acid | 0.1 | 1.08 | 0.704 | 0.883 | 1.0 |

TABLE 2b

| Test Compound | Concen-tration (mM) | Densitometer reading (average) | Standard Deviation | p-value (vs. control) | Fold increase over control |
|---|---|---|---|---|---|
| Control for ethylene glycol disuccinate and oxydisuccinate | | 0.755 | 0.0285 | | |
| Control for succinic acid, dioctyl sulfosuccinate, sulfosuccinic acid | | 0.540 | 0.0937 | | |
| Dioctyl sulfosuccinate | 0.1 | 0.410 | 0.0172 | 0.0338 | 0.8 |
| Dioctyl sulfosuccinate | 0.001 | 0.462 | 0.0247 | 0.160 | 0.9 |
| Succinic acid | 10 | 0.939 | 0.0454 | 0.000259 | 1.7 |
| Succinic acid | 1 | 0.859 | 0.0495 | 0.000953 | 1.6 |
| Sulfosuccinic acid | 10 | 0.901 | 0.0387 | 0.00389 | 1.7* |
| Sulfosuccinic acid | 1 | 0.532 | 0.0310 | 0.880 | 1.0 |
| Ethylene glycol disuccinate | 10 | 0.739 | 0.0604 | 0.634 | 1.0 |
| Ethylene glycol disuccinate | 1 | 1.15 | 0.131 | 0.00108 | 1.5* |
| Ethylene glycol disuccinate | 0.1 | 1.01 | 0.129 | 0.00841 | 1.3* |
| Oxydisuccinate | 10 | 0.680 | 0.151 | 0.363 | 0.9 |
| Oxydisuccinate | 1 | 0.883 | 0.118 | 0.809 | 1.2 |
| Oxydisuccinate | 0.1 | 0.616 | 0.125 | 0.0730 | 0.8 |

TABLE 2c

| Test Compound | Concen-tration (mM) | Densito-meter reading (average) | Standard Deviation | p-value (vs. control) | Fold increase over control |
|---|---|---|---|---|---|
| Control for ethylene glycol disuccinate, oxydisuccinate, and succinic acid | | 2.83 | 0.0897 | | |
| Control for sulfosuccinic acid | | 2.20 | 0.182 | | |
| Succinic acid | 10 | 1.76 | 0.213 | 0.000088 | 0.6 |
| Succinic acid | 1 | 1.38 | 0.259 | 0.000042 | 0.5 |
| Sulfosuccinic acid | 10 | 2.53 | 0.106 | 0.0226 | 1.1 |
| Sulfosuccinic acid | 1 | 2.66 | 0.103 | 0.00470 | 1.2* |
| Ethylene glycol disuccinate | 10 | 1.20 | 0.119 | 0.00000059 | 0.4 |
| Ethylene glycol disuccinate | 1 | 3.21 | 0.250 | 0.030 | 1.1* |
| Oxydisuccinate | 10 | 1.10 | 0.0715 | 0.000000087 | 0.4 |
| Oxydisuccinate | 1 | 2.41 | 0.368 | 0.0670 | 0.9 |

TABLE 2d

| Test Compound | Concen-tration (mM) | Densitometer reading (average) | Standard Deviation | p-value (vs. control) | Fold increase over control |
|---|---|---|---|---|---|
| Control for ethylene glycol disuccinate, oxydisuccinate, and succinic acid | | 1.10 | 0.0456 | | |
| Control for sulfosuccinic acid | | 1.10 | 0.0704 | | |
| Succinic acid | 10 | 1.16 | 0.0360 | 0.228 | 1.0 |
| Succinic acid | 1 | 1.08225 | 0.0894 | 0.709 | 1.0 |
| Sulfosuccinic acid | 10 | 1.33 | 0.0703 | 0.000468 | 1.3* |
| Sulfosuccinic acid | 1 | 1.48 | 0.122 | 0.000522 | 1.4* |
| Ethylene glycol disuccinate | 10 | 0.544 | 0.0599 | 0.000019 | 0.5 |
| Ethylene glycol disuccinate | 1 | 1.44 | 0.111 | 0.00219 | 1.3* |
| Oxydisuccinate | 10 | 0.577 | 0.0470 | 0.000016 | 0.5 |
| Oxydisuccinate | 1 | 1.35 | 0.0508 | 0.00144 | 1.2* |

It can be seen from the data in Tables 2a–2d that sulfosuccinate, oxydisuccinate and ethylene glycol disuccinate had significant effects on collagen synthesis by fibroblasts. Dioctyl sulfosuccinate, by contrast, was not effective in inducing collagen synthesis and succinic acid gave variable results.

It is evident from Examples 1 and 2 that the compounds claimed in this invention have the potential of delivering skin benefits by increasing collagen and GAGS which are known to be decreased in aging skin. Examples 3–8 illustrate topical compositions according to the present invention. The compositions can be processed in conventional manner. They are suitable for cosmetic use. In particular the compositions are suitable for application to wrinkled, rough, dry, flaky, aged and/or UV-damaged skin to improve the appearance and the feel thereof as well as for application to healthy skin to prevent or retard deterioration thereof.

EXAMPLE 3

This example illustrates a high internal phase water-in-oil emulsion incorporating the inventive composition.

|  | % w/w |
| --- | --- |
| Sulfosuccinic acid | 2 |
| Brij 92* | 5 |
| Bentone 38 | 0.5 |
| MgSO$_4$7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 4

This example illustrates an oil-in-water cream incorporating the inventive composition.

|  | % w/w |
| --- | --- |
| Ethylene glycol disuccinic acid | 4 |
| Mineral oil | 4 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)   Alfol 16RD is cetyl alcohol

EXAMPLE 5

This example illustrates an alcoholic lotion incorporating the composition according to the invention.

|  | % w/w |
| --- | --- |
| Oxydisuccinic acid | 5 |
| Ethanol | 40 |
| Perfume | qs |
| Butylated hydroxy toluene | 0.01 |
| Water | to 100 |

EXAMPLE 6

This example illustrates another alcoholic lotion containing the inventive composition.

|  | % w/w |
| --- | --- |
| Oxydisuccinic acid | 5 |
| Sulfosuccinic acid | 5 |
| Ethanol | 40 |
| Antioxidant | 0.1 |
| Perfume | qs |
| Water | to 100 |

EXAMPLE 7

This example illustrates a suncare cream incorporating the composition of the invention:

|  | % w/w |
| --- | --- |
| Ethylene glycol disuccinic acid | 6 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 8

This example illustrates a non-aqueous skin care composition incorporating the inventive combination.

|  | % w/w |
| --- | --- |
| Sulfosuccinic acid | 5 |
| Silicone gum SE-30[1] | 10 |
| Silicone fluid 345[2] | 20 |
| Silicone fluid 344[3] | 50.26 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

EXAMPLE 9

| OIL-IN-WATER EMULSION | | | |
| --- | --- | --- | --- |
| FULL CHEMICAL NAME OR CTFA NAME | % ACTIVE LEVEL IN FORMULATION | TRADE NAME AND % ACTIVE AS RECEIVED | SUPPLIER |
| disodium EDTA | 0.05 | Sequesterene Na2 | Ciba-Geigy |
| magnesium aluminum silicate | 0.6 | Veegum Ultra | Vanderbilt |
| methyl paraben | 0.15 | Methyl Paraben | Protameen |
| simethicone | 0.01 | DC Antifoam Emulsion | Dow Corning |
| butylene glycol 1,3 | 3.0 | Butylene Glycol 1,3 | Hoechst Celanese |
| hydroxyethylcellulose | 0.5 | Natrosol 250HHR | Aqualon |
| glycerine, USP | 2.0 | Glycerol USP | ViaChem |
| xanthan gum | 0.2 | Keltrol 1000 | Kelco/Merck |

OIL-IN-WATER EMULSION

| FULL CHEMICAL NAME OR CTFA NAME | % ACTIVE LEVEL IN FORMULATION | TRADE NAME AND % ACTIVE AS RECEIVED | SUPPLIER |
|---|---|---|---|
| triethanolamine | 1.2 | Triethanolamine 99% | Union Carbide |
| stearic acid | 3.0 | Pristerene 4911 | Unichema |
| propyl paraben NF | 0.1 | Propylparaben NF | Protameen Chemicals |
| glyceryl hydroxystearate | 1.5 | Naturechem GMHS | CasChem, Inc. |
| stearyl alcohol | 1.5 | Lanette 18DEO | Henkel |
| isostearyl palmitate | 6.0 | Protachem ISP | Protameen |
| $C_{12-15}$ alcohols octanoate | 3.0 | Hetester FAO | Heterene |
| dimethicone | 1.0 | Silicone Fluid 200 (50 cts) | Dow Corning |
| cholesterol NF | 0.5 | Cholesterol NF | Lancaster |
| sorbitan stearate | 1.0 | Sorbitan Stearate | Witco |
| butylated hydroxytoluene | 0.05 | Embanox BHT | Rhone Poulenc |
| tocopheryl acetate | 0.1 | Vitamine E Acetate | BASF |
| PEG-100 stearate | 2.0 | MYRJ 59 | ICI America |
| sodium stearoyl lactylate | 0.5 | Pationic SSL | RITA Corporation |
| hydroxycaprylic acid | 0.1 | Hydroxycaprylic Acid | Elida Gibbs - Germany |
| retinyl palmitate** | 0.06 | Vitamin A Palmitate 84% (1.7 M IU Vitamin A) | BASF |
| oxydisuccinate | 2.0 | | |
| water, DI | q.s. to 99.8 | | |
| alpha-bisabolol | 0.2 | Alpha-bisabolol | Dragoco |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin care composition comprising:
   (a) a succinate compound selected from the group consisting of sulfosuccinic acid or a salt thereof, 2,2'-oxydisuccinic acid or a salt thereof, ethylene glycol disuccininc acid or a salt thereof, and mixtures thereof in an amount of from about 0.5 to about 40 wt. %; and
   (b) a cosmetically acceptable vehicle.

2. A cosmetic method of improving the appearance of wrinkled, lined, dry, flaky, aged or photodamaged skin and improving skin thickness, elasticity, flexibility and plumpness, the method comprising applying to the skin the composition of claim 1.

3. A cosmetic method of increasing collagen synthesis by fibroblasts in human skin, the method comprising applying to the skin the composition of claim 1.

* * * * *